(12) United States Patent
Dowlatshahi

(10) Patent No.: US 7,171,253 B2
(45) Date of Patent: *Jan. 30, 2007

(54) APPARATUS AND METHOD FOR DELIVERING ABLATIVE LASER ENERGY AND DETERMINING THE VOLUME OF TUMOR MASS DESTROYED

(75) Inventor: Kambiz Dowlatshahi, Chicago, IL (US)

(73) Assignee: Kelsey, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/057,916

(22) Filed: Feb. 14, 2005

(65) Prior Publication Data
US 2005/0137467 A1    Jun. 23, 2005

Related U.S. Application Data

(63) Continuation of application No. 10/754,827, filed on Jan. 9, 2004, now Pat. No. 6,865,412, which is a continuation of application No. 10/263,639, filed on Oct. 3, 2002, now Pat. No. 6,701,175, which is a continuation of application No. 09/834,873, filed on Apr. 13, 2001, now Pat. No. 6,603,988.

(51) Int. Cl.
*A61B 5/05* (2006.01)
*A61B 6/00* (2006.01)
(52) U.S. Cl. .................. 600/407; 600/474; 600/476
(58) Field of Classification Search ............... 600/323, 600/407, 431, 436, 474, 476, 549, 1, 310, 600/322; 604/21; 606/11, 14–15, 42, 116; 607/96; 128/922
See application file for complete search history.

(56) References Cited

U.S. PATENT DOCUMENTS

| | | | |
|---|---|---|---|
| 4,961,422 A | * 10/1990 | Marchosky et al. | 607/99 |
| 5,078,142 A | 1/1992 | Siczek et al. | |
| 5,169,396 A | 12/1992 | Dowlatshahi et al. | |
| 5,178,148 A | 1/1993 | Lacoste et al. | |
| 5,178,164 A | * 1/1993 | Allen | 128/898 |
| 5,222,953 A | 6/1993 | Dowlatshahi | |

(Continued)

FOREIGN PATENT DOCUMENTS

JP    01148280    9/1989

(Continued)

OTHER PUBLICATIONS

Stereotactically Guided Laser Therapy of Occult Breast Tumors written by ARCH SURG, published Nov. 2000.

(Continued)

*Primary Examiner*—Tu Hoang
(74) *Attorney, Agent, or Firm*—Bell, Boyd & Lloyd LLC

(57) ABSTRACT

An apparatus and method for determining a volume of tumor mass destroyed. The present invention includes a temperature probe and a laser probe having a temperature sensor. The laser probe and temperature probe are inserted to measure a temperature of the tumor mass and a temperature of tissue mass surrounding the tumor mass. By determining the volume of tumor mass destroyed, a graphical representation of the volume of tumor mass destroyed is provided whereby real-time visual monitoring of the destruction of the tumor mass is achieved.

13 Claims, 10 Drawing Sheets
(2 of 10 Drawing Sheet(s) Filed in Color)

U.S. PATENT DOCUMENTS

| | | |
|---|---|---|
| 5,240,011 A | 8/1993 | Siczek et al. |
| 5,323,779 A * | 6/1994 | Hardy et al. .................. 600/411 |
| 5,415,169 A | 5/1995 | Siczek et al. |
| 5,520,182 A | 5/1996 | Leighton et al. |
| 5,569,240 A | 10/1996 | Dowlatshahi et al. |
| 5,735,264 A | 4/1998 | Siczek et al. |
| 5,813,985 A | 9/1998 | Carroll |
| 5,853,366 A | 12/1998 | Dowlatshahi |
| 6,023,637 A * | 2/2000 | Liu et al. .................... 600/474 |
| 6,241,725 B1 * | 6/2001 | Cosman ........................ 606/41 |
| 6,451,015 B1 * | 9/2002 | Rittman et al. ................ 606/34 |
| 6,498,942 B1 | 12/2002 | Esenaliev et al. |
| 6,603,988 B2 * | 8/2003 | Dowlatshahi ............... 600/407 |
| 6,701,175 B2 | 3/2004 | Dowlatshahi |
| 6,865,412 B2 | 3/2005 | Dowlatshahi |
| 2002/0026127 A1 * | 2/2002 | Balbierz et al. ............ 600/567 |

FOREIGN PATENT DOCUMENTS

| | | |
|---|---|---|
| JP | 2000237205 | 5/2000 |
| WO | 00/13603 | 3/2000 |
| WO | 005/59394 | 10/2000 |

OTHER PUBLICATIONS

International Search Report of Feb. 1, 2006 for International Appln. No. PCT/US02/11452 that corresponds to the present application.

* cited by examiner

APPARATUS AND METHOD FOR DELIVERING ABLATIVE LASER ENERGY AND DETERMINING THE VOLUME OF TUMOR MASS DESTROYED

PRIORITY CLAIM

This application is a continuation of and claims the benefit of priority to U.S. patent application Ser. No. 10/754,827 filed Jan. 9, 2004 now U.S. Pat. No. 6,865,412 which is incorporated herein in its entirety and which is a continuation of and claims the benefit of priority to Ser. No. 10/263,639, filed Oct. 3, 2002 now U.S. Pat. No. 6,701,175 issued on Mar. 2, 2004, which is a continuation of and claims the benefit of priority to Ser. No. 09/834,873, filed Apr. 13, 2001 now U.S. Pat. No. 6,603,988 issued on Aug. 5, 2003.

DESCRIPTION

The present invention relates in general to a method and apparatus for delivering ablative laser energy and determining the volume of tumor mass destroyed, and in particular to a method and apparatus for determining the volume of tumor mass destroyed by a minimally invasive treatment, such as interstitial laser therapy, such that a graphical representation of the destroyed tumor mass can be displayed for real-time visual monitoring of the destruction of tumor mass.

BACKGROUND OF THE INVENTION

Percutaneous in situ or on-site treatment of malignant breast tumors by laser therapy is being developed in part due to the fact that breast cancer is being detected at earlier stages because of the increasing number of women receiving mammograms annually. If breast cancer and other cancers or tumors are detected in early development, the tumor can be effectively treated using an ablative agent such as laser energy.

Image-guided laser treatments of malignant tumors such as, breast, liver, head and neck tumors, have been in development for more than a decade. For example, U.S. Pat. No. 5,169,396 ("the '396 patent") issued to Dowlatshahi is directed to the interstitial application of laser radiation therapy to tumor masses and is incorporated herein by reference. In general, the apparatus of the '396 patent includes a probe having a thin metallic cannula for insertion into a tumor mass, a laser for generating light having a chosen wavelength and intensity, and an optical fiber for receiving and transmitting the laser light to the tumor mass, whereby the optical fiber is inserted into the cannula such that a chosen physiologically acceptable fluid can flow coaxially between the cannula and the optical fiber. In addition, a heat sensing member is inserted adjacent into the tumor mass for monitoring the tumor temperature. The devitalized tumor is gradually cleared by the body immune system and within six months is replaced with a scar.

However, the treatment of tumors and in particular the specific treatment of breast tumors is generally known to be more difficult due to the fact that it is difficult to determine the three dimensional boundaries of the tumor, and thus, difficult to determine when all of the tumor has been destroyed.

To address this problem, medical researchers have utilized a variety of tumor mass identification techniques for determining the size and outer boundaries of a tumor mass. Examples of conventional identification techniques that have been employed in combination with laser therapy are magnetic resonance imaging, radiographic and sonographic techniques. When utilizing an identification technique, coordinates identifying the actual size of the tumor mass are determined by using stereotactic techniques or the like.

To solve this problem, at the time of laser treatment, markers may be placed in a 0.5–1.0 cm zone of "normal" tissue to demarcate the zone in which the tumor extension may exist. This ring of "normal" tissue is equivalent to a cuff of tissue engulfing the tumor removed during conventional surgery (i.e., a lumpectomy). The boundaries of the ring surrounding the tumor are marked at 3, 6, 9 and 12 o'clock locations by inserting metal markers through a needle. The insertion points are precisely determined by known stereotactic technique using a commercially available stereotactic table.

Such marker elements are the subject of U.S. Pat. No. 5,853,366 ("the '366 patent") issued to Dowlatshahi is directed to a marker element for interstitial treatment. In general, the '366 patent discloses a marker element that can be positioned wholly within the body of a patient by utilizing a guide member having a guide path so as to mark a tumor mass of interest. The marker element is made of a radiopaque material which includes any material that is capable of being detected by conventional radiographic, sonographic or magnetic techniques.

Medical researchers have also employed non-surgical techniques other than laser therapy to treat breast tumors. For example, radio frequency, microwave, and cryogenic-related treatments have been attempted.

The present invention recognizes the above described problem, that is, to provide a non-cutting treatment for cancer and in particular for breast cancer that can be relied upon to determine when the entire tumor is effectively destroyed. There is accordingly a need for a non-cutting breast cancer therapy which addresses this problem and the problems arising from the difficulty in determining whether the tumor is completely destroyed.

SUMMARY OF THE INVENTION

The present invention solves the above problems by providing an apparatus and method for determining a volume of tumor mass (such as breast cancer) destruction in tissue mass (such as breast tissue) within the body of a patient such that a graphical representation of the destroyed mass can be preferably superimposed onto an image of the actual tumor mass whereby the destruction of tumor mass can be visually monitored in real-time. The preferred embodiment of this invention is described in conjunction with breast tissue and breast cancer or tumors, although it should be appreciated that the present invention may be adapted to be implemented for other tumor or cancer treatment. The preferred embodiment of the present invention is also implemented with a patient positioned on a commercially available stereotactic table. The invention may alternatively be implemented using ultrasound and magnetic resonance imaging (MRI) techniques, provided that the tissue mass such as the breast is immobilized and the target is fixed.

The apparatus of one embodiment of the present invention preferably includes a laser gun. The laser gun is adapted to receive a laser probe having a temperature sensor thereon and a temperature probe having a series of temperature detectors thereon. The laser gun inserts the laser probe into the tumor mass to facilitate providing an effective amount of laser radiation and measuring the tumor temperature at the application point of the laser. The gun also subsequently inserts the temperature probe into the body preferably in close proximity of the tumor mass. The temperature probe measures the body or tissue temperature at various locations in proximity of the tumor mass during interstitial laser therapy. The laser probe and temperature probe preferably include position marks to enable the operator to precisely position and determine the position of the probes relative to each other.

The apparatus preferably includes a computer control system that is electrically connected to the laser gun and its components, namely, the laser probe and sensor and the temperature probe and detectors. The computer control system determines the volume of tumor mass destroyed by utilizing operational data, such as, the distance between the temperature sensors, temperature data, that the control system receives from the laser probe and temperature probe. The computer control system calculates the volume of tumor mass destroyed at any given time during the interstitial laser therapy based upon the tumor mass temperature and the body or tissue mass temperature surrounding the tumor mass.

As the computer control system calculates the volume of tumor mass destroyed, the computer control system displays sequential graphical representations of the amount of destroyed tumor mass which is superimposed onto an image of the actual tumor mass in real-time. This graphic display thereby enables doctors to visually monitor the amount of tumor mass destroyed in real-time during the interstitial laser therapy such that the user can determine when the tumor mass destruction is effectively complete.

It is therefore an advantage of the present invention to provide an apparatus and method for calculating the volume of tumor mass destruction such that a graphic representation of the destroyed tumor mass can be displayed.

It is another advantage of the present invention to provide real-time visual monitoring of the destruction of tumor mass during laser therapy.

It is a further advantage of the present invention to provide an apparatus and method for determining when the destruction of tumor mass is effectively complete.

It is still further an advantage of the present invention to provide an apparatus and method for determining when the destruction of a breast tumor mass is effectively complete during interstitial laser therapy.

Other objects, features and advantages of the present invention will be apparent from the following detailed disclosure, taken in conjunction with the accompanying sheets of drawings, wherein like reference numerals refer to like parts, components, processes and steps.

DESCRIPTION OF THE DRAWINGS

The patent or application file contains at least one drawing executed in color. Copies of this patent or patent application publication with color drawings will be provided by the Office upon request and payment of the necessary fee.

FIG. 5A illustrates blood flow prior to treatment without the aid of a contrasting agent. FIG. 5B illustrates blood flow prior to treatment with the aid of a contrasting agent. FIG. 5C illustrates the loss of blood flow after treatment.

DETAILED DESCRIPTION OF THE INVENTION

Figure 1A:
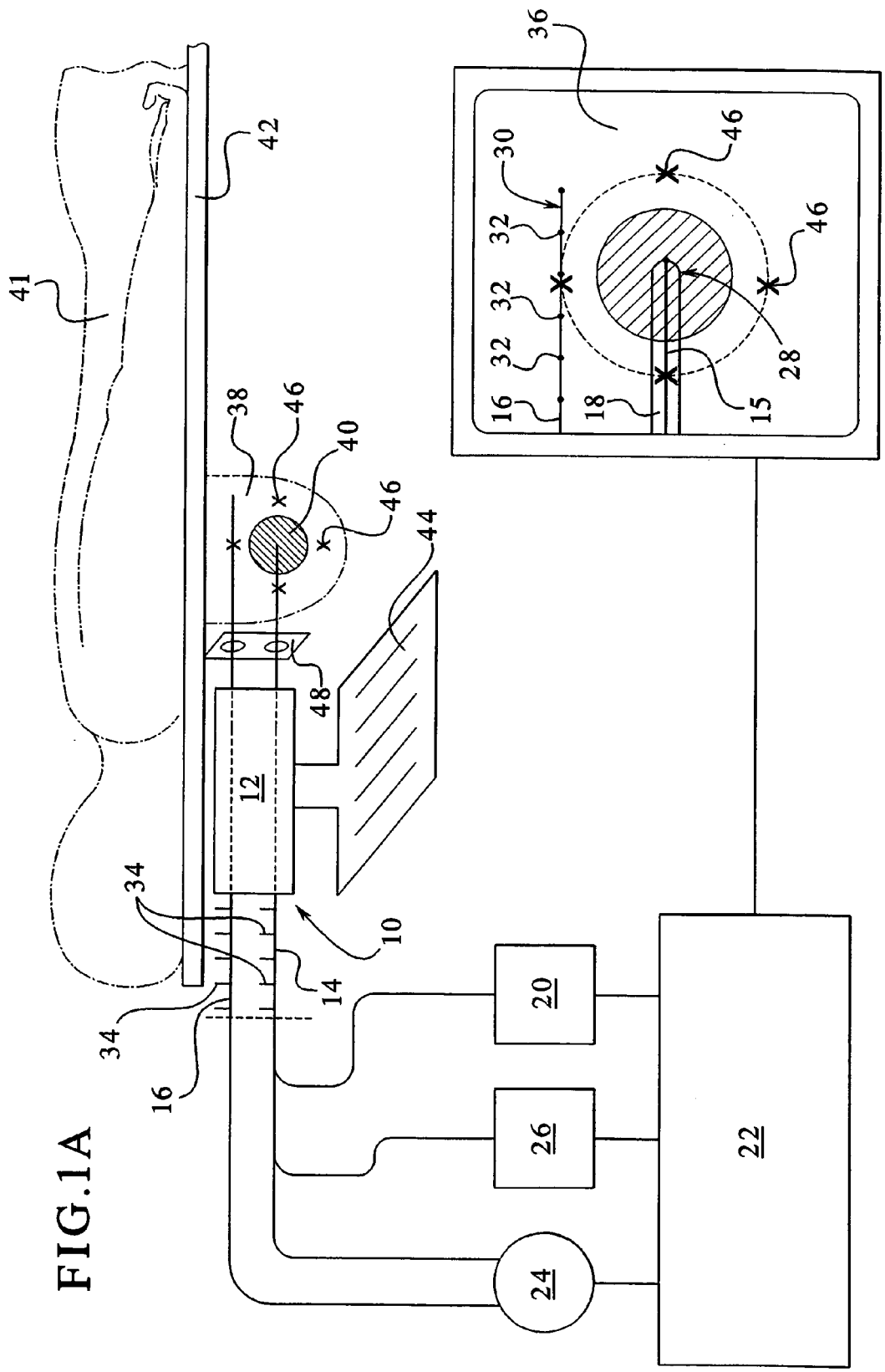
FIG. 1A is a perspective view of the apparatus of the present invention for determining the volume of tumor mass destroyed.

Referring now to the drawings, and particularly to FIGS. 1A, 1B, 2A and 2B, the apparatus and method for determining the volume of tumor mass destroyed is generally illustrated. The present invention provides a graphical display or representation of the volume of destroyed tumor mass by determining the volume of destroyed tumor mass based on the relative temperatures of the tumor mass and temperatures of tissue mass surrounding the tumor mass as described in detail below. This display preferably provides doctors or other operators with real-time visual monitoring of the destruction of tumor mass so as to determine when the destruction of the entire tumor mass is effectively complete.

The present invention monitors the temperature within and in close proximity to the tumor mass by utilizing a temperature sensor of the laser probe and a separate temperature probe having a number of temperature sensors or detectors. The temperature sensor and temperature probe provide temperature data for determining the volume of destroyed tumor mass, and thus, for providing the real-time graphical display of the destroyed tumor mass.

To calculate the destroyed tumor mass volume, the temperature probe must be positioned correctly relative to the temperature sensor and the relative distances therebetween must be accurately determined. The present invention utilizes a number of position marks located on the temperature probe and laser probe for positioning and for determining the relative positioning between the temperature detector and the laser probe as discussed below.

In an embodiment, the present invention preferably includes a laser gun 10 including a probe holder 12 employed during interstitial laser therapy. The probe holder 12 is adapted to receive a laser probe 14 and a temperature probe 16. The laser probe 14 and temperature probe 16 are removably inserted in and extend from the probe holder. The laser probe 14 and the temperature probe 16 are held in fixed position relative to each other by the gun. The positioning of the laser probe 14 and temperature probe 16 may be manual or computer controlled in accordance with the present invention.

The laser probe 14 includes a temperature sensor 15 and is adapted to receive an optical fiber 18 connected to a laser source 20 which is connected to a computer control system 22. The control system 22 is preferably connected to the temperature probe 16 and a temperature sensor 15 of the laser probe 14 via a temperature control device 24 so as to facilitate electrical connection with the computer control system 22. However, the laser probe 14 and temperature probe 16 can have separate control systems each connected to a central computer control system (not shown).

More specifically, the laser probe 14 includes a thin metallic cannula for insertion into the tumor mass and an optical fiber for receiving and transmitting the laser light or radiation to the tumor mass, whereby the optical fiber is inserted into the cannula such that a chosen physiologically acceptable fluid or anesthetic agent can flow between the cannula and the optical fiber as described in the '396 patent which is herein incorporated by reference as discussed above. In a preferred embodiment, the thin metallic cannula was approximately 18 centimeters in length and made from stainless steel ranging from 16 gauge to 18 gauge, but preferably 16 gauge. In addition, the optical or laser fiber is a quartz fiber ranging from 400 nanometers (nm) to 600 nm in diameter with a spherical tip. The optical fiber is commercially available, for example, from SURGIMED in Woodland, Texas.

Any suitable fluid pump 26 can be utilized to deliver the fluid such that the central temperature of the tumor does not exceed 100° C. or fall below 60° C. during laser therapy. In an embodiment, the fluid can be delivered at a rate ranging from 0.5 milliliters/minute (ml/min) to 2.0 ml/min.

The laser source 20 generates and supplies an effective amount of laser radiation to the laser probe 14. The laser source 20 is preferably a diode laser. In particular, the laser source 20 is a semiconductor 805-nanometer diode laser that is commercially available, for example, from Diomed in Cambridge, England. However, the present invention is not limited to the use of a diode laser and can utilize a variety of different and suitable laser sources.

The laser probe 14 also includes a temperature sensor 15 as previously discussed. The temperature sensor 15 is employed to effectively measure a temperature of the center of the tumor mass as the tumor mass is destroyed. The temperature sensor 15 is preferably attached directly by soldering or other like attachment mechanism to the laser probe 14 so as to measure the tumor mass temperature at a distal end 28 of the laser probe 14, preferably located at a center region of the tumor mass.

The distal end 30 of the temperature probe 16 is inserted into the body within the tissue mass of the body region that is in proximity of (i.e., preferably 1.0 cm away) and surrounds the tumor mass. The temperature probe 16 includes a series of temperature detectors 32 or sensors that are positioned at various distances or intervals (i.e., preferably 0.5 cm) along the temperature probe. In a preferred embodiment, the temperature probe 16 is made from stainless steel ranging from 16 gauge to 20 gauge, preferably 16 gauge. As further illustrated in FIG. 3, the temperature detectors 32 of the temperature probe 16 are positioned at T1, T2, T3, T4 and T5. Based on this configuration, tissue mass temperature measurements are taken at various distances away from the tumor mass surface. This temperature data is utilized in conjunction with the relative distances of the temperature sensors to calculate the volume of tumor mass destroyed, and therefore is utilized to determine when the entire tumor mass is effectively destroyed as discussed below.

As previously discussed, the relative positioning of the temperature probe 16 to the laser probe 14 must be determined in order to accurately calculate the volume of tumor mass destroyed. As shown in FIG. 1A, the temperature probe 16 and laser probe 14 include a number of position marks 34 in order to determine the relative positions of the temperature probe 16 and laser probe 14. The position marks 34 are preferably evenly spaced apart along a portion of a length of the temperature probe 16 and along a portion of the length of the laser probe 14 at a preferable distance of 0.5 cm. However, the present invention is not limited to this distance and can include position marks spaced apart at a variety of different positions. The operator can use these position marks to correctly position the laser probe and the temperature probe relative to the laser probe.

The present invention preferably includes the computer control system 22 adapted to electronically connect to the laser gun 10 and its components, namely, the temperature probe and the laser probe 14 having the temperature sensor 15. The computer control system 22 receives data from the laser probe 14 and the temperature probe 16 as the tumor mass is heated and destroyed. The data is utilized to calculate the volume of tumor mass destroyed at any given point in time. This calculation is based upon the temperature data from the temperature probe 16 and temperature sensor 15. The computer control system 22 utilizes the destroyed tumor volume calculations for graphically depicting the volume of tumor mass destroyed (i.e., tumor mass destruction zone) on a display 36 connected to the computer control system 22.

In one embodiment, the laser gun 10 injects the laser probe 14 and temperature probe 16 into breast tissue 38 in order to destroy a tumor mass 40 located within the breast tissue 38 of a patient 41 lying on an examination table 42. The laser gun 10 is positioned on a stereotactic platform or table 44 which is utilized in a conventional manner to identify the actual location of the tumor mass 40 in the breast tissue 38 prior to insertion of the temperature probe 16 and laser probe 14 into the breast tissue 38. In a preferred embodiment, the stereotactic platform or table 44 is commercially available from LORAD/Trex Medical Stereoguide DSM of Danbury, Conn. However, this identification can be performed using conventional radiographic, sonographic, thermographic, magnetic imaging or other like identification techniques.

After the tumor mass 40 location is identified, a number of marker elements 46 are preferably inserted into the breast tissue 38 in close proximity of the breast tumor 40. The marker elements 46 are utilized for marking the tumor mass 40 to be treated and to allow subsequent identification and observation of the treated area as further described in the '366 patent herein incorporated by reference as previously discussed.

By knowing the actual location of the tumor mass, the laser gun 10 can be configured to inject the laser probe 14 and temperature probe 16 into the breast tissue 38 at an optimal location relative to the tumor mass 40 in the breast tissue 38. The present invention utilizes a probe guide 48 to facilitate the insertion of the temperature probe 16 and laser probe 14 into the breast tissue 38. The positioning of the laser probe 14, temperature probe 16 and marker elements 46 relative to the positioning of the tumor mass 40 and tissue mass surrounding the tumor mass can be visually monitored on the display 36.

Figure 1B:
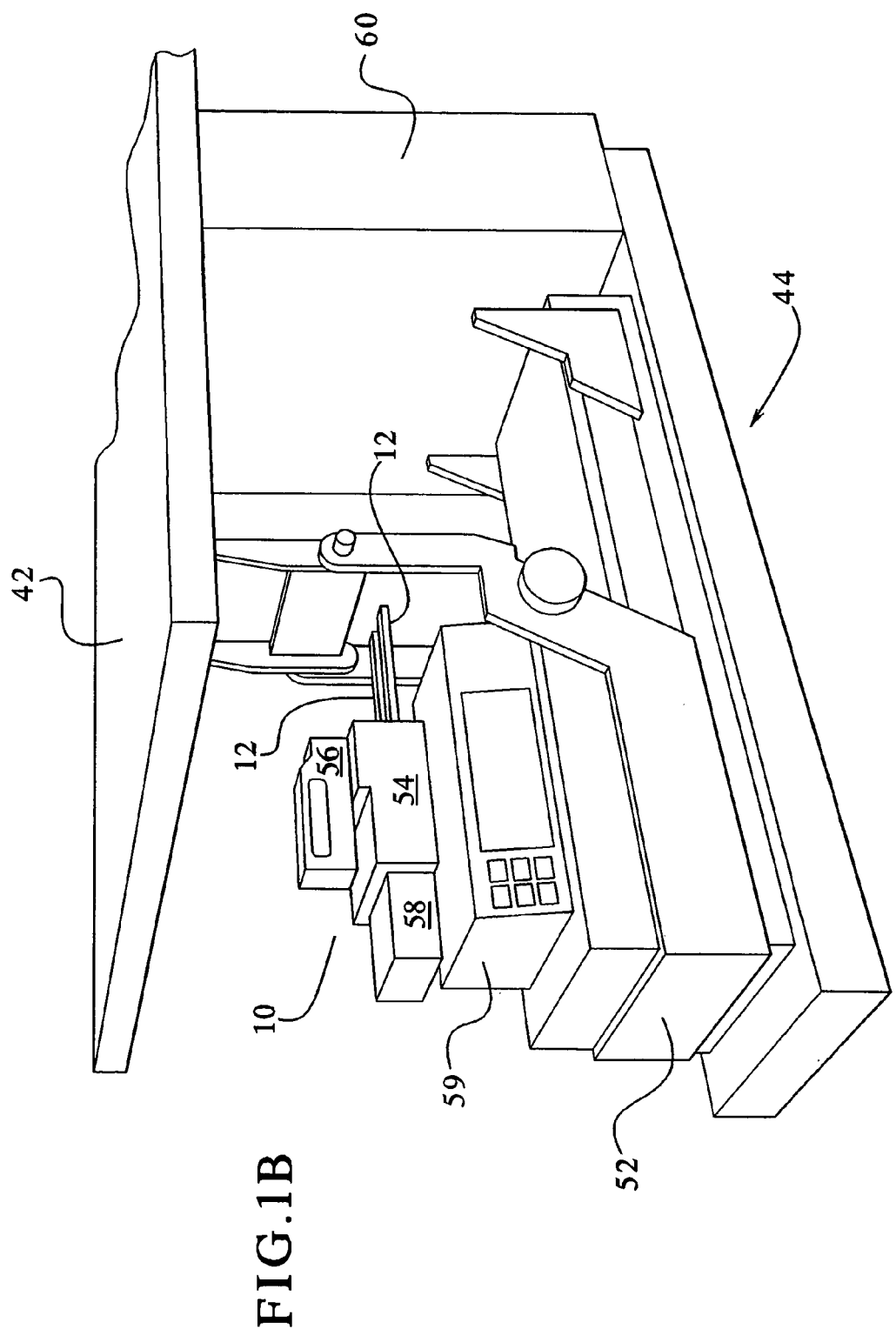
FIG. 1B is a perspective view of the apparatus of the present invention which illustrates the laser gun.

As previously discussed, the present invention utilizes a laser gun 10 to inject the laser probe 14 and temperature probe 16 into the tumor mass and tissue mass surrounding the tumor mass. The laser gun 10 can be made of any suitable material and be constructed in a variety of different configurations. One example of such configuration is illustrated in FIG. 1B.

The laser gun 10 is positioned on a guide mechanism 52 of the stereotactic table 44 which enables the laser gun 10 to be positioned prior to insertion of the laser probe and temperature probe. The laser gun 10 includes a housing 54 for the laser probe and temperature probe and probe holders 12 which can extend from the housing for each of the laser probe and temperature probe. The laser gun 10 further includes an alignment member 56 attached to the housing for aligning the laser gun prior to insertion. The laser gun 10 can also include an inserter member 58 attached to the housing for automatically inserting the laser probe and temperature probe. The laser gun 10 is connected to a control system 59 which includes a computer processing unit 60. The control system 58 operates to control and monitor the temperature probe and laser probe during laser therapy, such as controlling the laser source and fluid pump and monitoring the temperature.

Figure 2A:
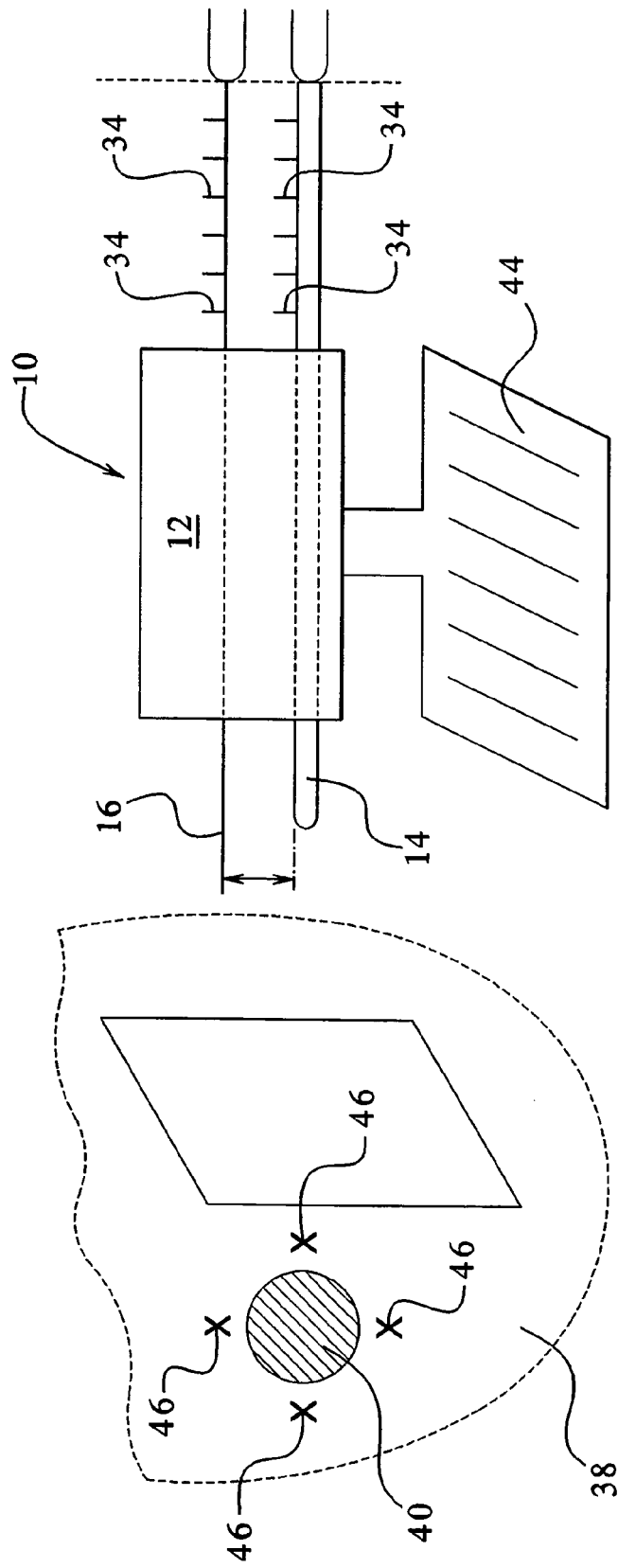
FIG. 2A is a schematic diagram of the laser probe and temperature probe prior to insertion into the tissue mass or body containing the tumor mass.
Figure 2B:
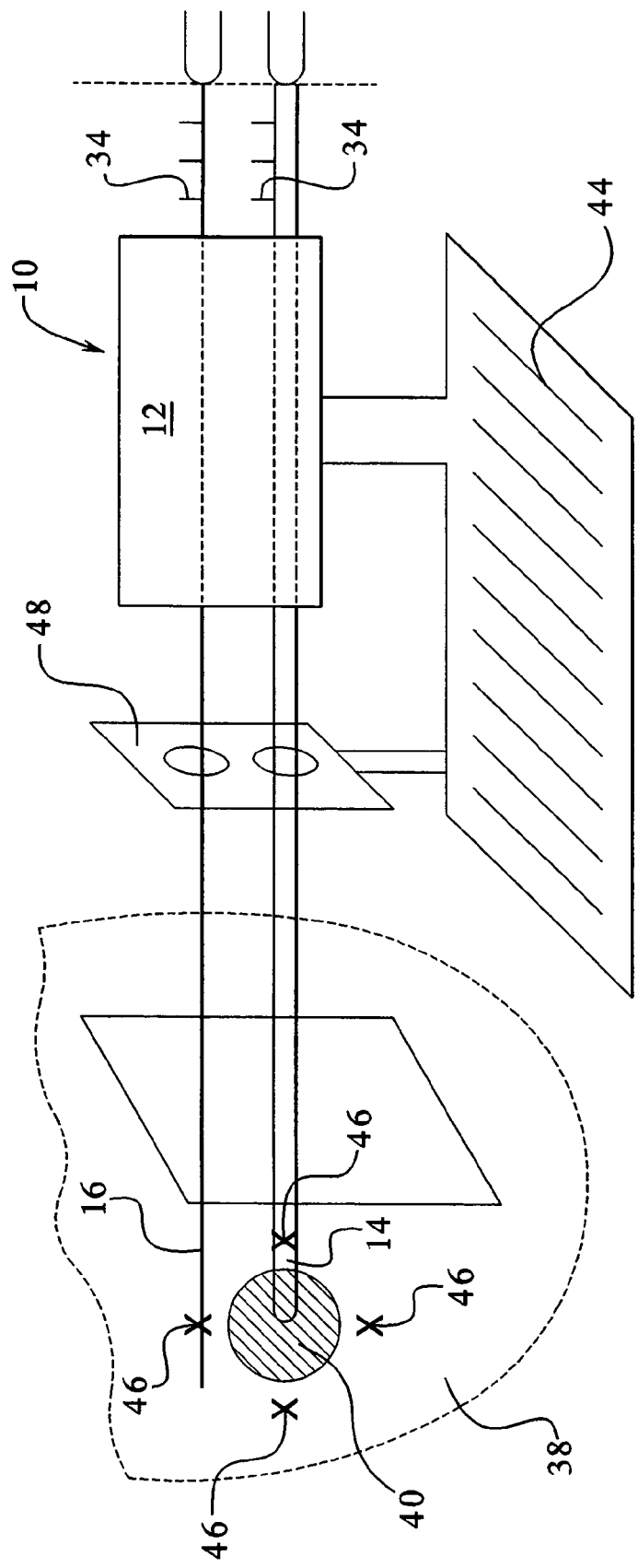
FIG. 2B is a schematic diagram of the laser probe and temperature probe inserted into the tissue mass containing the tumor mass.

The laser probe 14 is first optimally inserted into the center of the tumor mass as shown in FIG. 2B. Once the laser probe 14 is optimally inserted into the tumor mass 40, the temperature probe 16 is optimally inserted and positioned parallel to the laser probe 14 (i.e., preferably approximately 1 cm away from the laser probe) as further illustrated in FIGS. 2A and 2B. The optimal locations of the temperature probe 16 and laser probe 14 are necessary to monitor a concentric zone of heat emitted from the tip of the laser probe during treatment. As discussed below, the ability to monitor the concentric heat patterns of the laser probe is necessary to effectively measure the volume of tumor mass destroyed during treatment.

Because of the importance placed on the exact and precise positioning of the laser probe 14 and temperature probe 16 relative to the tumor mass 40, the present invention preferably utilizes the stereotactic technique in combination with the marker elements to monitor this positioning. The present invention further utilizes a plurality of position marks 34 located on each of the temperature probe 16 and laser probe 14 for monitoring the axial positioning of the laser probe 14 relative to the temperature probe 16. As previously discussed, the position marks 34 are spaced apart at known distances, preferably 0.5 cm, along each of the temperature probe 16 and laser probe 14. Therefore, the position marks 34 are utilized to visually monitor the relative positioning of the laser probe 14 and temperature probe 16 such that manual adjustments in addition to computer automated adjustments can be made to the relative positioning of the laser probe 14 and temperature probe 16.

Figure 3:
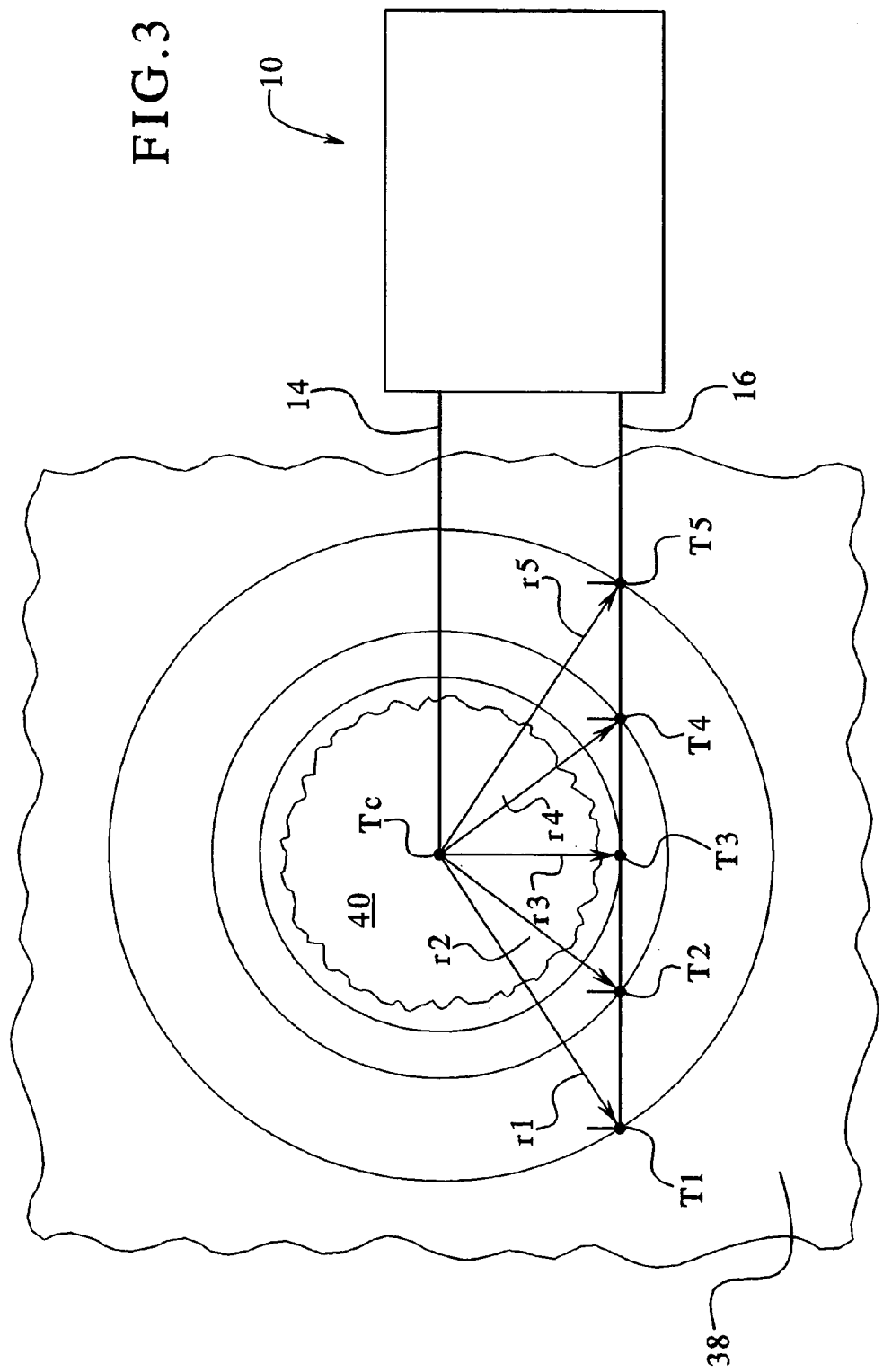
FIG. 3 is a schematic diagram of the laser probe and temperature probe illustrating the relationship of the volume of tumor mass destroyed with respect to the temperature sensor of the laser probe and the temperature detectors of the temperature probe.

As shown in FIG. 3, the temperature probe 16 preferably includes a temperature detector T3 that contacts an outer surface of the tumor mass 40 to measure a temperature at this location. The remaining temperature detectors, namely, T1, T2, T4 and T5 are positioned at the distances (described above) from T3 along the temperature probe. Each temperature detector is also located at various radial distances from the temperature sensor Tc (i.e., the temperature at the center of the tumor mass) of the laser probe 14, namely, r1, r2, r3, r4 and r5. The radial distance between Tc and T3 (i.e., r3) is known, that is, the axial distance between Tc and T3, preferably 1.0 cm. By knowing the distances between T3 and the other temperature detectors (i.e., T1, T2, T4 and T5) and the radial distance between T3 and Tc, the radial distance from Tc to each of T1, T2, T4 and T5 can be determined by applying the Pythagorean theorem, that is, for a right angled triangle having a hypotenuse length H and side lengths A and B defining the right angle, the relationship $H^2 = A^2 + B^2$ exists.

For example, $(r1)^2 = (T1-T3)^2 + (r3)^2 = (1.0 \text{ cm})^2 + (1.0 \text{ cm})^2 = 2.0 \text{ cm}^2$ where T1−T3=1.0 cm and r3=1.0 cm. Therefore, $r1 = r5 = (2.0 \text{ cm}^2)^{1/2} = 1.4$ cm. Based on similar calculations, r4=r2=1.10 cm where T1 −T2=0.5 cm and r3=1.0 cm. Therefore, the tissue temperature surrounding the tumor relative to the temperature at the laser fiber tip, i.e., Tc, can be monitored by the temperature detectors, such as T1, T2, T3, T4 and T5, at various known and corresponding radial distances from the laser fiber tip, such as r1=1.4 cm, r2=1.10 cm, r3=1.0 cm, r4=1.10 cm and r5=1.4 cm as previously discussed.

By determining the radial distances, volume calculations are made at each of the temperature detector locations preferably based upon the known calculation for a volume of a sphere V, that is $V = 4/3 \Pi r^3$, where r is the radial distance from the center of the sphere and $\Pi$ is the universally accepted constant value of 22/7, that is, the value of the ratio of the circumference of any circle relative to its diameter. When the temperature at any one of the temperature detectors reaches a level at which the tumor mass is destroyed, the volume calculation at each of the temperature detectors effectively corresponds to the volume of tumor mass destroyed within the spherical region having a radial distance associated with the temperature detector(s), namely, r1, r2, r3, r4 and r5.

For example, when the laser radiation is first applied, the tumor mass 40 is destroyed in a region at and near Tc. As time passes, the volume of tumor mass destroyed increases in correlation to an increase in the temperature as measured by T3. Therefore, the volume of tumor mass destroyed is effectively less than the volume corresponding to the spherical region having a radial distance of r3.

When T3 reaches or increases to a temperature, preferably 60° C., which would destroy the tumor mass, that is, the tumor mass destruction temperature, the volume of tumor mass destroyed effectively corresponds to the volume of a spherical region having a radial distance of r3. The spherical shape of the destroyed tumor mass has been documented on rodent mammary tumors and thirty-six patients with breast cancer whose laser treated tumors were serially removed and sectioned by pathologists and reported.

To ensure that the entire tumor mass is effectively destroyed, the laser treatment continues until the temperatures as measured by the other or outer temperature detectors, namely, T1, T2, T4 and T5, reach or increase to the tumor mass destruction temperature, preferably 60° C. When this occurs, the tumor mass is effectively destroyed within the volume of the spherical region having a radial distance associated with the outer temperature detectors, namely, r1, r2, r4 and r5. The laser treatment ends when a temperature as measured by the outermost temperature detector(s), such as T1 and T5, increases to the tumor mass destruction temperature, preferably 60° C.

It should be appreciated that the amount of laser energy which is necessary to destroy the tumor mass and the tissue mass surrounding the tumor mass can also be determined. Based on previous studies conducted by the inventor, the destruction of approximately 1 cm$^3$ of tumor mass and/or tissue mass surrounding the tumor mass requires approximately 2500 Joules (J) of laser energy. (See, for example, Dowlatshahi et al., *Stereotactically Guided Laser Therapy of Occult Breast Tumors*, ARCH. SURG., Vol. 135, pp. 1345–1352, November 2000). By calculating the amount of tumor mass destroyed and assuming that the amount of tumor mass destruction requires approximately 2500J/cm$^3$ of laser energy, the amount of laser energy (J) which is necessary to destroy the volume of tumor mass can be calculated.

It should be appreciated that the present invention is not limited to the number, type, positions, and locations of the temperature detectors. A variety of locations and number of detectors may be utilized depending, for example, on the tumor treatment conditions, such as, the type and location of the tumor. In a preferred embodiment, the temperature detectors are positioned to effectively monitor the destruction of tumor mass to a radial distance from the actual tumor mass associated with the outer temperature detectors (i.e., T1 and T5).

It should also be appreciated that the present invention is not limited to the tumor mass destruction temperature. A variety of different temperatures may be utilized to correspond to the tumor mass destruction temperature depending on the tumor treatment conditions as described above. In a preferred embodiment, the preferred tumor mass destruction temperature is at least 60° C.

Figure 4A:
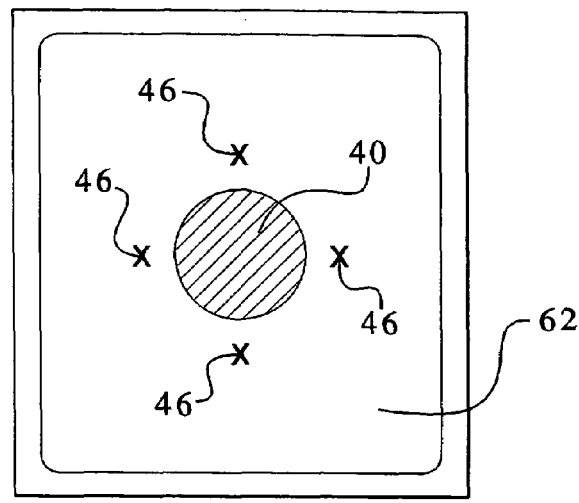
FIGS. 4A to 4C illustrate the graphically superimposed tumor mass destruction zone at a beginning, subsequent and final stages of laser therapy for visual real-time monitoring of the destruction of the tumor mass.

The computer control system utilizes the tumor mass destruction calculation(s) as described above to provide a graphic display 62 or representation of the destroyed tumor mass that is preferably superimposed onto an image of the actual tumor mass taken prior to treatment as illustrated in FIG. 4A. The graphic display 62 of the destroyed tumor mass is preferably displayed as a circular (2-D) or spherical (3-D) symbol. The marker elements are also graphically displayed in addition to the tumor mass.

Figure 4B:
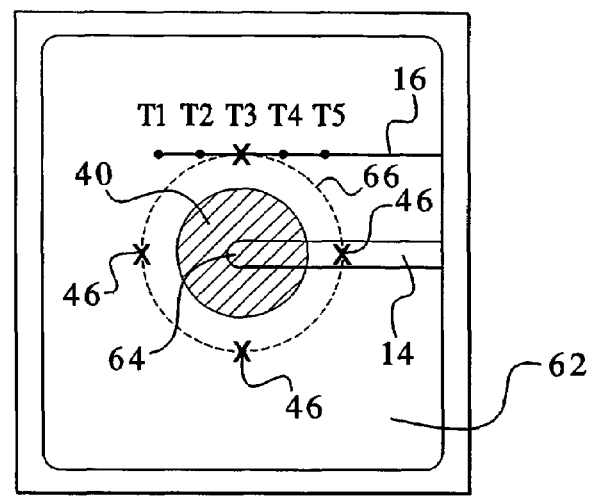
Figure 4C:
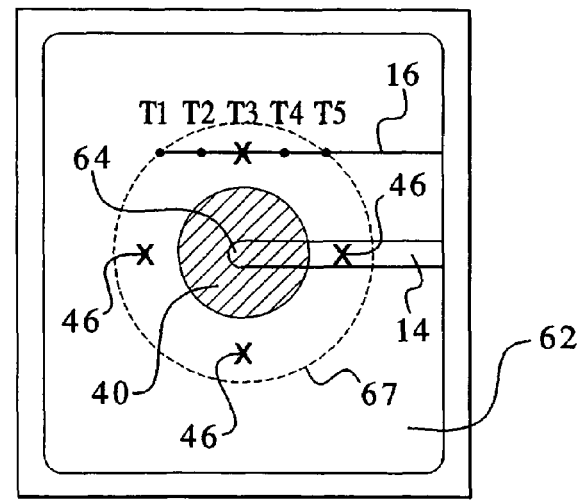

In FIG. 4B, the display 62 illustrates the laser probe 14 and temperature probe 16 after insertion into the breast tissue. The tip 64 of the laser probe 14 is centrally located within the tumor mass 40, and the temperature probe 16 is positioned relative to the laser probe 14 as previously discussed. As the temperature increases spatially and concentrically away from the tip of the laser probe, the temperature detector at T3 measures a tumor mass destruction temperature (i.e., preferably 60° C.). At this temperature, the destroyed tumor mass symbol 66 appears as illustrated in the display of FIG. 4B. As the temperature at T1 and T5 reach the tumor mass destruction temperature, the destroyed tumor mass symbol 67 expands to include the destroyed tumor mass region associated with T1 and T5 as shown in FIG. 4C.

The tumor mass destruction symbol extends outwardly from the actual image of the tumor mass by a distance associated with the location of the outer temperature detectors of the temperature probe (i.e., T1 and T5). At this distance, the tumor mass destruction is effectively complete as further illustrated in FIG. 4C. This distance ranges from about 0.25 cm to about 0.75 cm, preferably ranging from about 0.4 cm to about 0.5 cm. The graphic display of the present invention provides a real-time visual monitoring of the destruction of tumor mass in contrast to known displays that only illustrate the temperature at various locations of the tumor mass by a conventional bar graph.

Figure 4D:
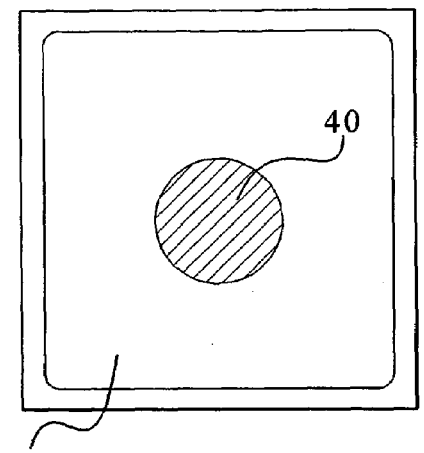
FIGS. 4D to 4H illustrate alternative graphical representations of the tumor mass destruction zone at beginning, subsequent and final stages of laser therapy for visual real-time monitoring of the destruction of the tumor mass.
Figure 4E:
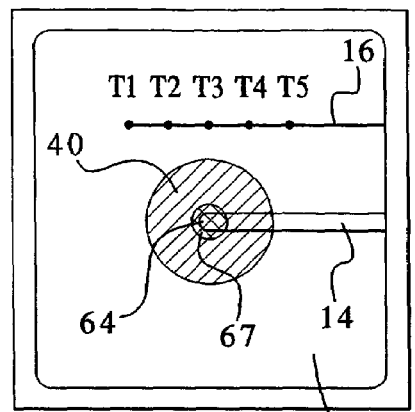
Figure 4F:
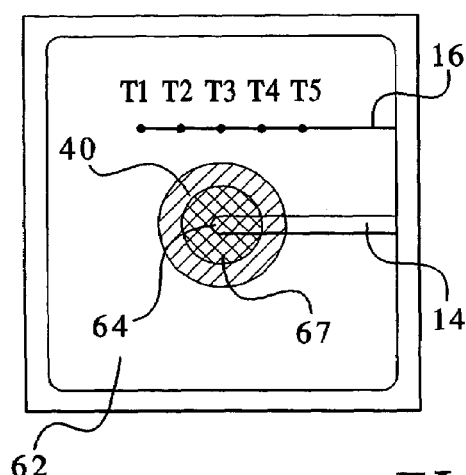
Figure 4G:
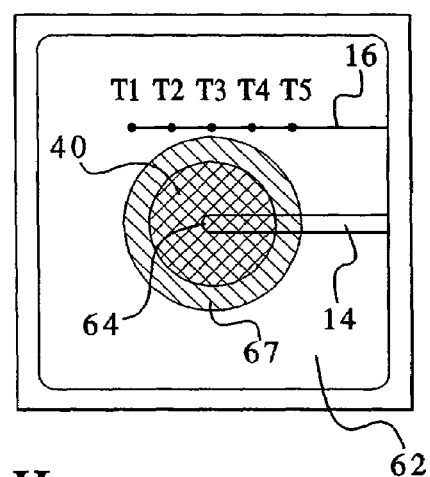
Figure 4H:
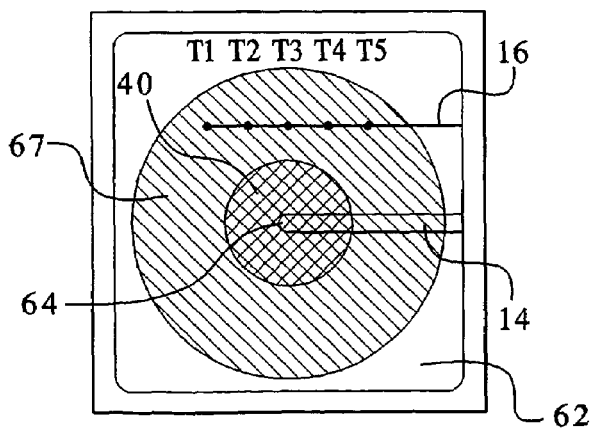

An alternative embodiment of the graphical representations of the tumor mass destruction zone at the beginning, subsequent and final stages of laser therapy for visual real-time monitoring of the destruction of the tumor mass is illustrated in FIGS. 4D, 4E, 4F, 4G and 4H. FIG. 4D illustrates the tumor without any destruction zone. FIGS. 4E, 4F, 4G and 4H illustrates the destruction zone increasing in size to expand beyond the tumor zone. It should be appreciated that different cross hatching, shading and graphical images can be used to graphically illustrate the tumor mass and the destruction zone. It should also be appreciated that different colors can be graphically used to illustrate the tumor mass and the destruction zone.

Figure 4I:
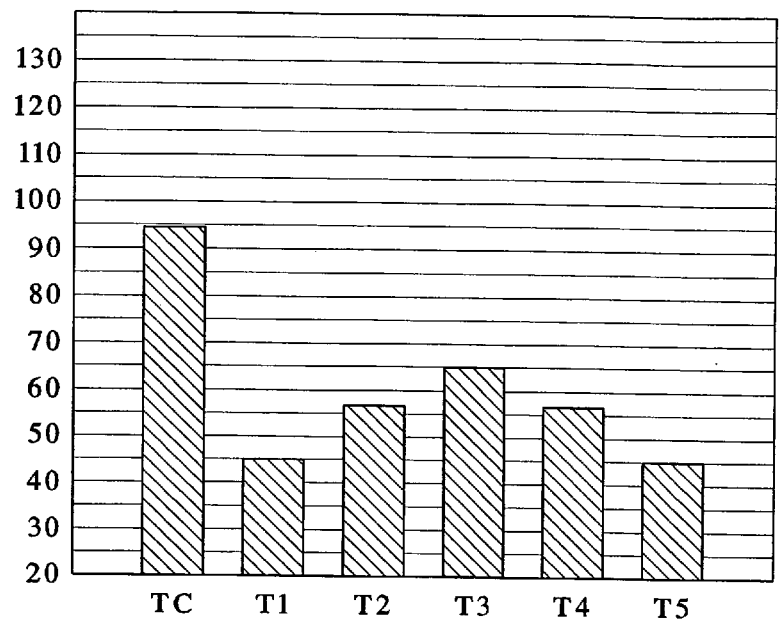
FIGS. 4I and 4J illustrate a further alternative graphical bar representation of the temperature at Tc, T1, T2, T3, T4 and T5 at different stages of the destruction of the tumor mass.
Figure 4J:
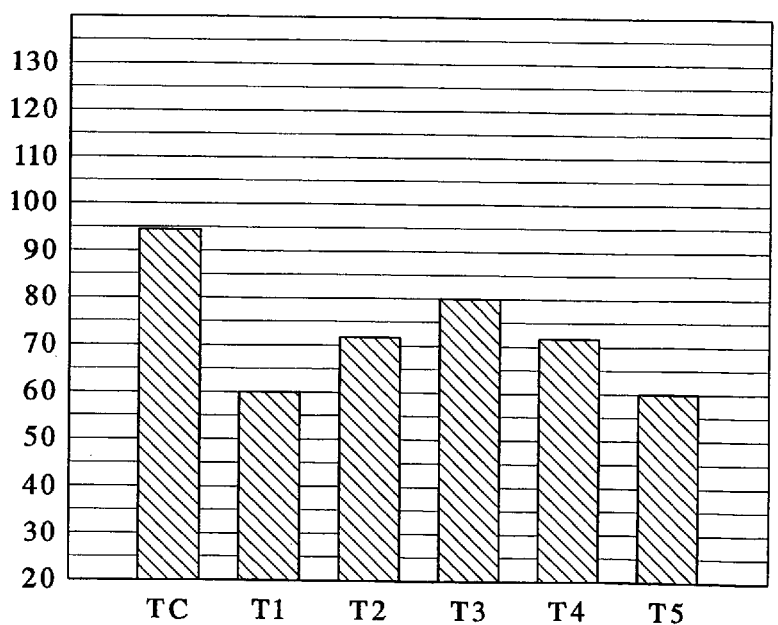

It should further be appreciated that a further graphical representation of the temperatures could be implemented in conjunction with the above mentioned graphical images. FIGS. 4I and 4J illustrate a bar graph which is preferably also provided to the operator of the system. The bar graphs show the temperature at Tc, T1, T2, T3, T4 and T5 at different points in time. As illustrated in FIG. 4I, the temperature at Tc is much greater than the temperature at T3, which is greater than the temperature at T2 and T4, which is greater than the temperature at T1 and T5. As the tumor mass destruction temperature increases at these points and the destruction zone increases, the bar graph changes to a point in time as illustrated in FIG. 4J. At this point, the areas at T1 and T5 are above the tumor mass destruction temperature which is preferably 60° C. Therefore, the operator knows that the mass has been destroyed in addition to the graphical representations described above.

In an alternative embodiment, the present invention utilizes a blood circulation test in combination with real-time visual monitoring to determine when the destruction of the entire tumor mass is effectively complete. Any suitable blood circulation test can be utilized. However, contrast-enhanced color doppler ultrasound is the preferred technique that utilizes a suitable contrasting agent and a suitable transducer ultrasound for observing blood with color as it circulates in the tumor mass and tissue mass (i.e., breast tissue) surrounding the tumor mass. The blood circulation test is conducted before and after treatment and the results are compared to determine whether the tumor mass was effectively destroyed.

Any suitable transducer and contrasting agent may be utilized. In a preferred embodiment, the transducer ultrasound is a 7.5 MHz linear array transducer ultrasound that is commercially available from ATL in Bothel, Wash.

In addition, the contrasting agent is preferably a sonicated albumin-based agent, that is, an albumin-based material having gas-injected bubbles. It should be appreciated that the reflection of sound waves from the bubbles within the albumin-based material produces a color response indicative of blood flow or circulation. In particular, the contrasting agent is OPTISON which is a commercially available product from Mallinkrodt of St. Louis, Mo.

Figure 5A:
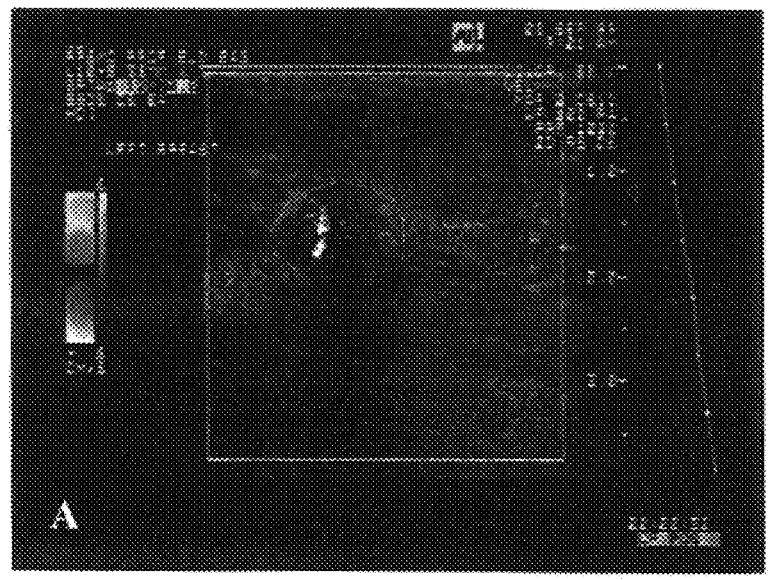
FIGS. 5A, 5B and 5C illustrate blood flow within the tumor mass and tissue mass surrounding the tumor mass before and after treatment as measured by color doppler ultrasound.

Before treatment, an effective amount of the contrasting agent is preferably injected into a vein. The contrasting agent is utilized to enhance the image of blood circulation that results from the color doppler ultrasound technique. The effectiveness of the contrasting agent is shown by comparing the color doppler ultrasound blood flow images of FIGS. 5A and 5B. The contrasting agent was utilized to produce the blood flow image of FIG. 5B and not FIG. 5A. By comparing these figures, it is evident that the blood flow image of FIG. 5B is more enhanced than the blood flow image of FIG. 5A.

Figure 5B:
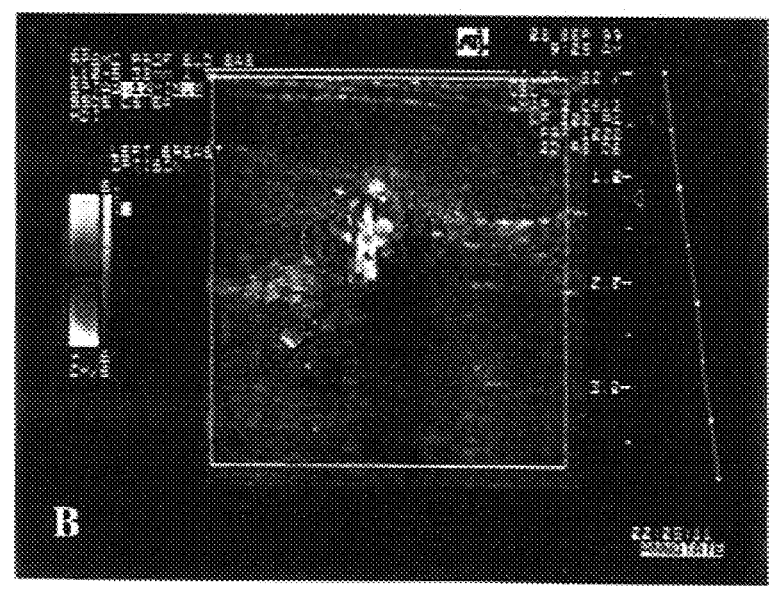
Figure 5C:
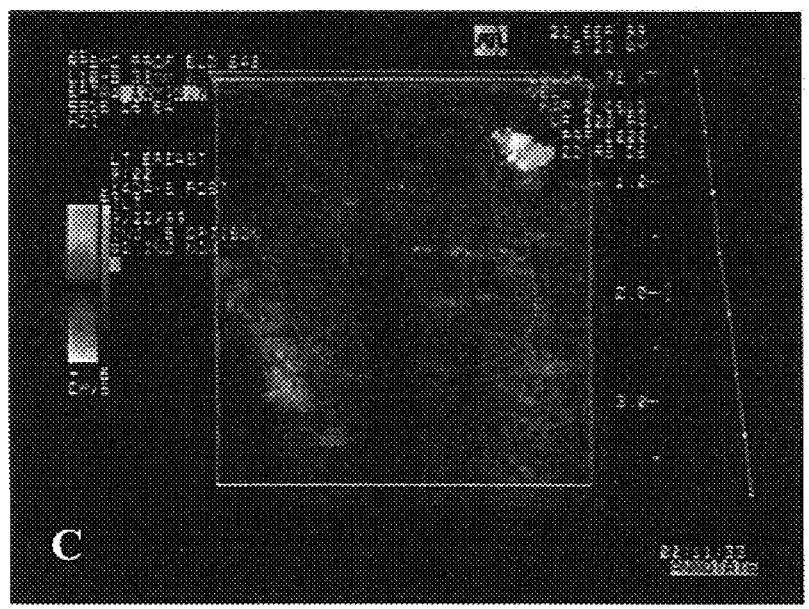

Turning to FIG. 5B, the contrast-enhanced color doppler ultrasound measured a substantial amount of blood flow within the tumor mass and tissue mass surrounding the tumor mass. After treatment, the contrasting agent is again injected to observe blood flow in and around the tumor mass. As further predicted, there was effectively no blood flow within the tumor mass and surrounding area as measured by the above-described ultrasound technique as shown in FIG. 5C. This indicates that the tumor mass and tissue mass surrounding the tumor mass was effectively destroyed. If the tumor mass and the surrounding tissue mass has been destroyed, blood circulation in this treated region effectively cannot be observed by color doppler ultrasound. A comparative analysis between the results of the blood circulation test before and after treatment is utilized to make the determination as to whether the entire tumor mass is destroyed.

This change in blood circulation in and around the tumor mass can also be observed by injecting an effective amount of the contrasting agent into the vein during laser therapy. This provides real-time monitoring of the blood circulation within the tumor mass and tissue mass surrounding the tumor mass during laser treatment. As more and more of the tumor mass and surrounding tissue mass is destroyed, less blood circulates through this region. As the blood circulation decreases, the blood circulation test, such as the color doppler ultrasound, can be utilized to effectively measure a decrease in blood circulation as previously discussed. A graphical representation of the results of the color doppler ultrasound can be continuously monitored during laser therapy. The graphical representation can be displayed on a separate display or can be superimposed onto the actual image of the tumor mass during laser therapy. The graphical representation provides further real-time monitoring of tumor destruction before the patient is removed from the table. Additional laser treatment can be delivered if a portion of the targeted tissue exhibits blood flow suggesting viability. It should be appreciated that the graphical representation can be configured in any suitable way such that the blood flow circulation can be monitored.

Figure 6:
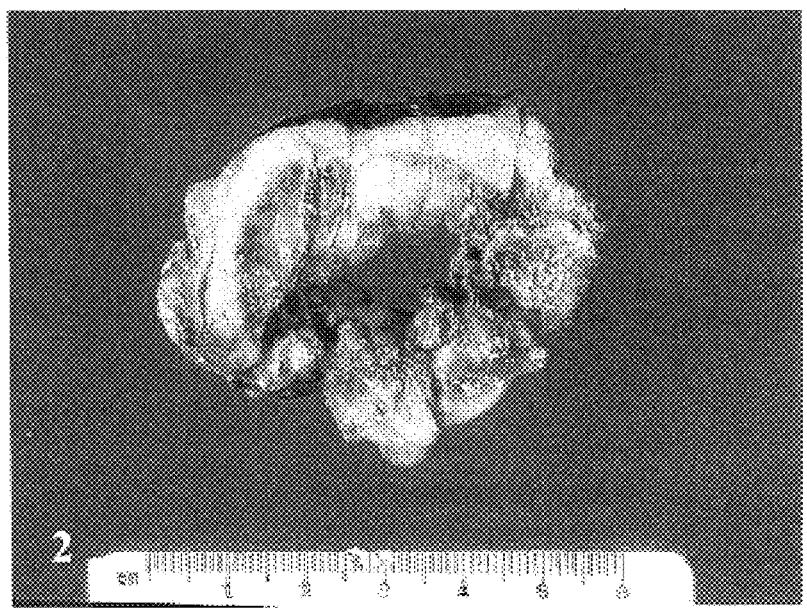
FIG. 6 is a photograph that illustrates an actual tumor mass destroyed from laser therapy of the present invention.

An actual tumor mass that has been destroyed during laser therapy of the present invention is illustrated in FIG. 6. The void region represents the region where the tumor mass and surrounding tissue mass were destroyed by laser therapy. As shown in FIG. 6, the void region is effectively circular in shape and has an approximate diameter of 2.5 to 3.0 cm. FIG. 6 illustrates a cut section of a laser treated breast tumor. The red ring is the inflammatory zone and the tissue within it is destroyed. The diameter of this ring corresponds to the diameter of the avascular zone seen by color Doppler ultrasound in FIG. 5C.

The present invention also provides a method for determining the volume of tumor mass destroyed. The method preferably includes the step of providing a laser gun. The laser gun further includes a laser probe and temperature probe as detailed above. The laser probe and temperature probe are inserted into the body of the patient such that the laser probe is inserted into the tumor mass and the temperature probe is inserted into the tissue mass in proximity to the tumor mass. An effective amount of laser radiation is generated and directed into the tumor mass through the laser probe. The temperature sensor of the laser probe measures the tumor mass temperature within the tumor mass. The temperature probe measures the tissue temperature of tissue mass surrounding the tumor mass at various positions along the temperature probe. The computer control system is preferably electronically connected to the laser gun and its components, namely the laser probe, the temperature sensor of the laser probe, and the temperature probe, and a fluid pump. The computer control system receives temperature and laser data from the temperature and laser probes for determining or calculating a volume of tumor mass destruction as detailed above. The computer (or operator) adjusts the fluid flow delivered by the fluid pump so that the central temperature of the tumor, i.e., Tc, does not exceed 100° C. or fall below 60° C. during laser therapy.

The computer control system utilizes this calculation to create a display that graphically superimposes the destroyed tumor mass onto the image of the actual tumor mass. By graphically showing the amount of tumor mass destroyed, the doctor can visually monitor the destruction of tumor mass under real-time so as to determine when the destruction of tumor mass is effectively complete as detailed above.

In an alternative embodiment, the method of the present invention includes the step of identifying the tumor mass prior to insertion of the laser gun into the tumor mass. The identification step is performed using conventional radiographic, sonographic or magnetic imaging techniques. Preferably, coordinates identifying the actual location of the tumor mass are determined using stereotactic techniques or the like as previously discussed.

In another alternative embodiment, the present invention utilizes a blood circulation test, such as color doppler ultrasound, before and after treatment to provide further evidence when the entire tumor mass is effectively destroyed as previously discussed. The blood circulation test can also be utilized during laser therapy to provide further real-time monitoring of the tumor mass destruction as further discussed above.

It should be appreciated that the present invention is not limited to interstitial laser therapy, and particularly, interstitial laser therapy for the destruction of a breast tumor. The present invention may apply to a variety of different non-surgical treatments for the destruction of a variety of different tumor masses.

It should be understood that modifications and variations may be effected without departing from the scope of the novel concepts of the present invention, and it should be understood that this application is to be limited only by the scope of the appended claims.

The invention is claimed as follows:

1. An apparatus displaying a volume of a tumor mass destroyed, the apparatus comprising:

means for measuring a temperature of at least part of the tumor mass;

means for measuring at least a temperature at one point in proximity of the tumor mass; and means for providing a graphical representation of the volume of the tumor mass destroyed based at least in part upon measuring temperature of at least part of the tumor mass and at least one point in proximity of the tumor mass.

2. The apparatus of claim 1, wherein the graphical representation of the volume of the tumor mass destroyed is superimposed onto an image of the tumor mass to provide real-time visual monitoring of the destroyed tumor mass.

3. The apparatus of claim 2, wherein the graphical representation includes a geometrical symbol.

4. An apparatus for determining a volume of tumor mass destroyed, the apparatus comprising:

a laser probe having a temperature sensor operable to measure a temperature of said tumor mass;

a computer control system electrically connected to the laser probe and operable to determine the volume of tumor mass destroyed based upon the tumor mass temperature and a tissue temperature measured in proximity to the tumor mass;

a display connected to the computer control system and operable to display a graphical representation of the volume of tumor mass destroyed; and means for conducting a blood circulation test employing a contrasting agent to determine the volume of the tumor mass destroyed by an amount of laser energy.

5. An apparatus displaying a volume of a tumor mass destroyed, the apparatus comprising:

means for measuring a temperature of at least part of the tumor mass;

means for measuring at least a temperature at one point in proximity of the tumor mass; and means for providing a graphical representation of the volume of the tumor mass destroyed based at least in part upon measuring temperature of at least part of the tumor mass and at least one point in proximity of the tumor mass, wherein the graphical representation of the volume of the tumor mass destroyed is superimposed onto an image of the tumor mass to provide real-time visual monitoring of the destroyed tumor mass, and wherein the real-time visual monitoring of the destroyed tumor mass is provided during interstitial laser therapy.

6. The apparatus of claim 5, which includes means for conducting a blood circulation test employing a contrasting agent to determine the volume of the tumor mass destroyed.

7. The apparatus of claim 6, wherein the blood circulation test includes a contrast-enhanced color doppler ultrasound test.

8. The apparatus of claim 7, wherein the blood circulation test confirms that an entire amount of the tumor mass is effectively destroyed.

9. The apparatus of claim 8, wherein the blood circulation test is conducted before and after the tumor mass is destroyed.

10. An apparatus displaying a volume of a tumor mass destroyed, the apparatus comprising:

means for measuring a temperature of at least part of the tumor mass;

means for measuring at least a temperature at one point in proximity of the tumor mass;

means for providing a graphical representation of the volume of the tumor mass destroyed based at least in part upon measuring temperature of at least part of the tumor mass and at least one point in proximity of the tumor mass; and means for conducting a blood circulation test employing a contrasting agent to determine the volume of the tumor mass destroyed.

11. The apparatus of claim 10, wherein the blood circulation test includes a contrast-enhanced color doppler ultrasound test.

12. The apparatus of claim 11, wherein the blood circulation test confirms that an entire amount of the tumor mass is effectively destroyed.

13. The apparatus of claim 12, wherein the blood circulation test is conducted before and after the tumor mass is destroyed.

* * * * *